United States Patent [19]

Schwartz, deceased

[11] Plant 5,101

[45] Sep. 13, 1983

[54] MINIATURE ROSE PLANT—SCHANBIRAN VARIETY

[75] Inventor: Earnest Schwartz, deceased, late of Kingsville, Md., by Hazel E. Schwartz, executrix

[73] Assignee: The Conard-Pyle Company, West Grove, Pa.

[21] Appl. No.: 313,663

[22] Filed: Oct. 21, 1981

[30] Foreign Application Priority Data

Oct. 22, 1980 [NL] Netherlands ..... ROO 1034

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided which often bears a single bloom per stem having an attractive pink and white tonality. The new variety originated by the crossing of an unnamed and unpatented Miniature rose seedling with the variety Ma Perkins (U.S. Plant Pat. No. 1,143), a Floribunda whose parentage was the variety Red Radiance (unpantented) crossed with the variety Fashion (U.S. Plant Pat. No. 789).

2 Drawing Figures

SUMMARY OF THE INVENTION

The present variety relates to a new and distinct variety of rose plant of the Miniature Class which was originated by me by crossing an unnamed and unpatented Miniature rose seedling with a Floribunda rose named Ma Perkins (U.S. Plant Pat. No. 1,143). The parentage of Ma Perkins variety was the variety Red Radiance (unpatented) crossed with the variety Fashion (U.S. Plant Pat. No. 789).

As the result of this breeding, I have produced a new and distinct rose variety of the Miniature Class which is distinguished from its parents, as well as from all other varieties of which I am aware, as evidenced by the following unique combination of characteristics which are outstanding therein:

(a) a vigorous growth habit, (b) the common formation of an attractive single bloom per stem having a distinctive pink and white tonality, and (c) the formation of dark green foliage which covers the plant well having above average resistance to the common garden diseases.

Asexual reproduction of the new variety by budding and by cuttings, as performed at West Grove, Pa., shows that the aforementioned characteristics and distinctions come true to form and are established and transmitted through succeeding propagations.

The new variety has been named the Schanbiran variety.

BRIEF DESCRIPTION OF THE PHOTOGRAPH

The accompanying photographs show typical specimens of the vegetative growth and flowers of my new variety in different stages of development cultivated in the outdoors at West Grove, Pa. as depicted in color as nearly true as it is reasonably possible to make the same in color illustrations of this character. FIG. 1 was obtained during August 1981, and FIG. 2 was obtained during October 1982.

DETAILED DESCRIPTION OF THE DISCLOSURE

Figure 1:
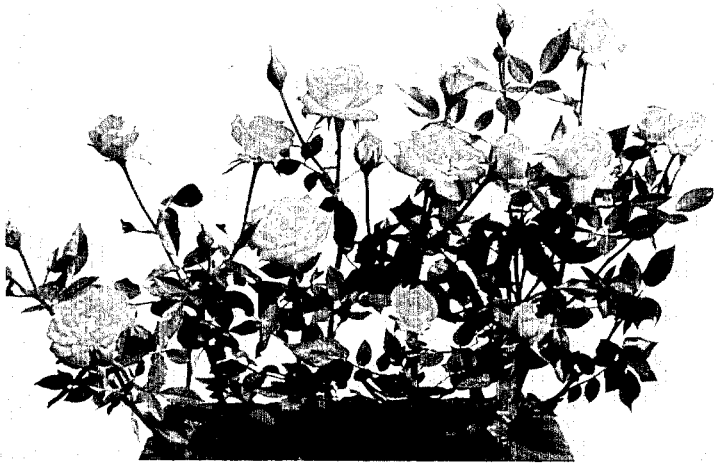
Figure 2:
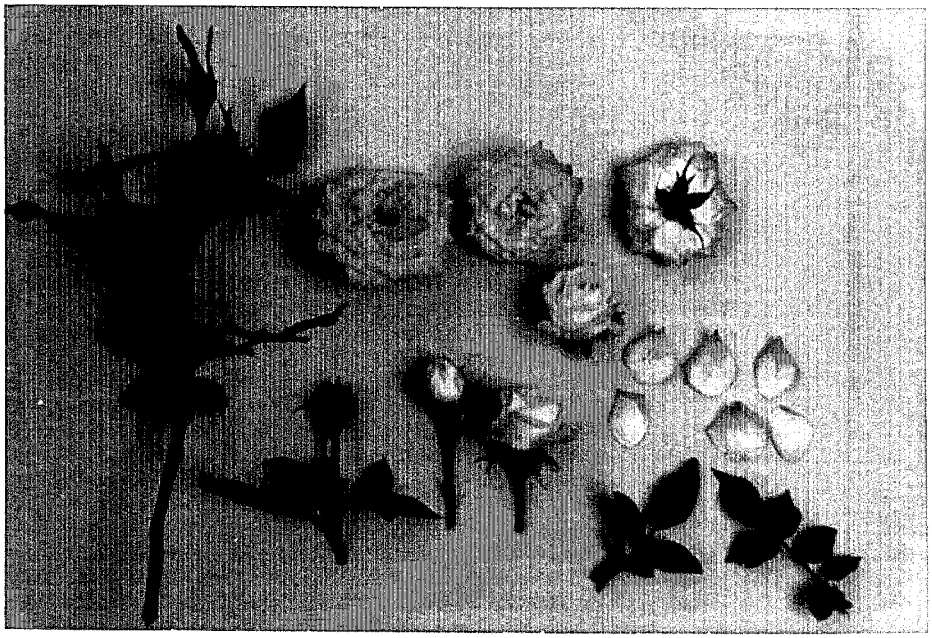

The plants described were grown outdoors at West Grove, Pa.

The chart used in the identification of the colors is that of The Royal Horticultural Society (R.H.S. Colour Chart).

Class: Miniature.

Branches:

*Color.*—New shoots, Green Group 138B with reddish overcast bearing foliage of Greyed-Red Group 181A. Young stems, dull, Greyed-Purple Group 185C mixed with Green Group 137C. Main stems, dull, Green Group 137C.

*Thorns.*—Young stems, few and reddish in color. Main stems, present in moderate amounts.

Foliage:

*Leaves.*—Usually composed of 7 to 9 leaflets, moderately large for the Class, cover plant exceptionally well.

*Leaflets.*—Lanceolate in shape having an acuminate apex, an obtuse base, and a serrulate margin. Color: young foliage: upper surface: Yellow-Green Group 147B to 147C. Under surface: Yellow-Green Group 148B to 148C. Color: mature foliage: Upper surface: Yellow-Green Group 147A. Under surface: Yellow-Green Group 148B.

Flowers:

*Number of flowers.*—Commonly one per stem, sometimes 3 or 4 per stem.

*Quantity of bloom.*—Abundant outdoors.

*Fragrance.*—None.

*Continuity.*—Continuous.

Penduncle.—Average length of approximately 2.4 to 3.7 cm.

*Sepals.*—Permanent, short to medium length, spear shaped.

*Bud.*—Shape: ovoid with a conspicuous neck, with foliaceous appendages on the surface of the bud, with slender foliaceous parts extending beyond the tip of the bud equal to one-fourth or more of its length. Size: average length of approximately 8 to 12 mm. before calyx breaks. Color: as calyx breaks: Red Group 53C with base of petal Yellow-White Group 158C mixed with Yellow Group 11D. Color: as first petal opens: the point of attachment and basal quarter of petal is Yellow-Green Group 1D, remainder of petal is shades of Red Group 51A through 51D with a margin of Red Group 53D.

*Flower.*—Size when fully open: average from approximately 2.4 to 4.5 cm., but occasionally larger. Petalage: double, average from approximately 22 to 30 petals, arranged regularly. The petals are broadly ovate, satiny on the inside and outside, and medium soft in texture. The top edges of the outer petals are recurved forming a point. Form: high centered at first but becoming flat, petals at first loosely recurved and remaining loosely recurved at maturity. Color: three-quarters open, outer petal — outside surface: base and middle of petal Yellow-White Group 158C changing to Red Group 52B. Tip of petal Red Group 53C. Color: three-quarters open, outer petal — inner surface: base of petal Yellow-White Group 158C blending to Yellow Group 158D. Tip of petal Red Group 53C with tones of Red Group 53D. Color: three-quarters open, intermediate petal — outside surface: base of petal Yellow Group 2D blending to Yellow Group 8D with shades of Yellow-White Group 158D. Outer tip of petal Red Group 53C with shades of Red Group 53D. Color: three-quarters open, intermediate petal — inner surface: base of petal Yellow Group 5D changing to Red Group 52A. Tip of petal Red Group 53C. Color: three-quarters open, inner petal — outside surface: base of petal Green-Yellow Group 1D changing to Yellow Group 2D. Outer edges and tip of petal blending from Red Group 52B to 53C. Color: three-quarters open, inner petal — inner surface: base of petal Yellow Group 3D changing to Yellow Group 4D with shades of Yellow Group 5D. Inside tip of petal Red Group 52C changing to Red Group 53C with shades of Red Group 53D. Color: fully open three days, outer petal — outside surface: base White Group 155D ranging to White Group 155B. Upper part of petal Red Group 51A with tip ranging from Red Group 53C to 53D. Color: fully open three days, outer petal — inner surface: base White Group 155B blending at upper part of petal Red Group 51A with tip Red Group 53C. Color: fully open three days, inner petal — outside surface: base White Group 155B changing to Red Group 51B with tones of 51A. Tip of petal Red Group 53C to 53D. Color: fully open three days, inner petal — inner surface: base White Group 155B changing to Red Group 51B with tones of Red Group 53C and 53D. General color effect: the general effect of a fully open bloom is Red Group 51B and White Group 155B. Flower longevity: on the bush in garden approximately 4 to 7 days from calyx break to color breakdown and dropping off of petals. Stamens: medium number, arranged irregularly about pistils, mixed with petaloids. Filaments: short, some with anthers, Yellow-Green Group 153C in color. Anthers: very small, occasionally fused with petaloid, Yellow Group 5C with shades of Red Group 52B in color. Pistils: medium number. Styles: uneven, short columnar. Stigma: Yellow-Green Group 153D in color. Hips: none observed. Seeds: none observed.

Disease resistance: Resistance slightly above average under the same cultural conditions.

Growth:

*Habit.*—Dwarf; upright.

*Growth.*—Free.

*Canes.*—Light.

Usage: The new variety is particularly suited for use as a garden decoration and for pot forcing.

I claim:

1. A new and distinct variety of rose plant of the Miniature Class, substantially as herein shown and described, characterized particularly by a vigorous growth habit, the common formation of an attractive single bloom per stem having a distinctive pink and white tonality, and the formation of dark green foliage which covers the plant well having above average resistance to common garden diseases.

* * * * *